(12) United States Patent
Basiony

(10) Patent No.: US 10,010,718 B2
(45) Date of Patent: Jul. 3, 2018

(54) DEVICE TO KILL MICRO-ORGANISMS INSIDE THE RESPIRATORY TRACT

(71) Applicant: Mohamed A Basiony, Kenmore, WA (US)

(72) Inventor: Mohamed A Basiony, Kenmore, WA (US)

(*) Notice: Subject to any disclaimer, the term of this patent is extended or adjusted under 35 U.S.C. 154(b) by 0 days.

(21) Appl. No.: 15/471,882

(22) Filed: Mar. 28, 2017

(65) Prior Publication Data

US 2017/0281966 A1  Oct. 5, 2017

Related U.S. Application Data

(60) Provisional application No. 62/390,486, filed on Apr. 1, 2016.

(51) Int. Cl.
*A61M 16/00* (2006.01)
*A62B 9/06* (2006.01)
*A61N 5/06* (2006.01)
*A61M 16/04* (2006.01)

(52) U.S. Cl.
CPC ....... *A61N 5/0603* (2013.01); *A61M 16/0463* (2013.01); *A61M 16/0486* (2014.02); *A61N 5/0624* (2013.01); *A61M 2202/0208* (2013.01); *A61N 2005/0604* (2013.01); *A61N 2005/0626* (2013.01); *A61N 2005/0651* (2013.01); *A61N 2005/0661* (2013.01)

(58) Field of Classification Search
CPC .......... A61M 16/0486; A61M 16/0463; A61N 5/0603; A61N 5/0624

USPC ....................................... 128/207.14–207.15
See application file for complete search history.

(56) References Cited

U.S. PATENT DOCUMENTS

| 5,637,877 A * | 6/1997 | Sinofsky .................. A61L 2/10 250/492.1 |
| 7,159,590 B2 * | 1/2007 | Rife ....................... A61M 16/04 128/200.26 |
| 2002/0165594 A1 * | 11/2002 | Biel .................... A61K 41/0057 607/89 |
| 2004/0158302 A1 * | 8/2004 | Chornenky ............ A61B 18/24 607/94 |
| 2005/0279354 A1 * | 12/2005 | Deutsch ................... A61B 1/07 128/200.24 |
| 2007/0187626 A1 * | 8/2007 | Gaska ....................... A61L 2/10 250/504 R |
| 2010/0222852 A1 * | 9/2010 | Vasily .................. A61N 5/0603 607/89 |
| 2011/0023885 A1 * | 2/2011 | Vazales ............. A61B 1/00142 128/207.14 |

(Continued)

*Primary Examiner* — Kristen Matter
(74) *Attorney, Agent, or Firm* — James Haugen; Seattle Patent Group LLC

(57) ABSTRACT

A present idea relates to a device to kill micro-organisms inside the patient's respiratory tract using UV light, specifically UV-C. It is particularly used to treat patients with Coronaviruses family such as Severe Acute Respiratory Syndrome (SARS) and Middle East Respiratory Syndrome (MERS). The device consists of a triple-lumen catheter and UV control unit. The distal end of one of the catheter's lumen has a curved UV chamber while the proximal end has a cable with a socket to be connected to the UV control unit. The second lumen of the catheter is used for oxygen supply, and the third lumen of the catheter is used for suction.

4 Claims, 3 Drawing Sheets

(56) References Cited

U.S. PATENT DOCUMENTS

2013/0025602 A1\* 1/2013 Hayman ........... A61M 16/0434
  128/207.15
2013/0104884 A1\* 5/2013 Vazales .................. A61B 1/267
  128/202.16

\* cited by examiner

US 10,010,718 B2

DEVICE TO KILL MICRO-ORGANISMS INSIDE THE RESPIRATORY TRACT

FIELD

The instant application generally relates to a device to kill micro-organisms inside a patient's respiratory tract using UV light, specifically UV-C. It is particularly used to treat patients with Coronaviruses family such as Severe Acute Respiratory Syndrome (SARS) and Middle East Respiratory Syndrome (MERS).

BACKGROUND

Healthline and Medline Plus (U.S. National Library of Medicine, have published the following related to Severe Acute Respiratory Syndrome (SARS). Severe acute respiratory syndrome (SARS) is a serious form of viral pneumonia caused by the SARS coronavirus. The virus that causes SARS was first identified in 2003.

The World Health Organization has designated SARS a global health threat. Breathing issues will appear within two to 10 days after a person is exposed to the virus. Health officials will quarantine a person who presents the above symptoms and family members if they have a history of foreign travel. The person will be quarantined for 10 days to prevent the virus from spreading.

SARS can spread when an infected person sneezes, coughs, or comes into face-to-face contact with someone else. SARS can cause complications as most of the fatalities associated with SARS result from respiratory failure. SARS can also lead to heart and liver failure.

There is no confirmed treatment that works for every person who has SARS.

Antiviral medications and steroids are sometimes given to reduce lung swelling, but aren't effective for everyone. Supplemental oxygen or a ventilator may be prescribed if necessary. In severe cases, blood plasma from someone who has already recovered from SARS may also be administered. However, there is not yet enough evidence to prove that these treatments are effective.

The Mayo Clinic has published that in spite of a concerted global effort, scientists have yet to find an effective treatment for SARS. Antibiotic drugs don't work against viruses, and antiviral drugs haven't shown much benefit The World Health Organization has published the following related to Middle East respiratory syndrome (MERS).

Middle East respiratory syndrome (MERS) is a viral respiratory disease caused by a novel coronavirus (MERS-CoV) that was first identified in Saudi Arabia in 2012.

Typical MERS symptoms include fever, cough, and shortness of breath. Pneumonia is common, but not always present. Gastrointestinal symptoms, including diarrhea, have also been reported. Approximately 36% of reported patients with MERS have died. No vaccine or specific treatment is currently available. Treatment is supportive and based on the patient's clinical condition. There is no effective treatment for both SARS and MERS; for that reason, this idea may support the current efforts to treat such diseases caused by Coronaviruses family and any others diseases caused by the other viruses and Bacteria.

SUMMARY

Ultraviolet is a means of killing or rendering harmless micro-organisms (Viruses and Bacteria) in a dedicated environment. Ultraviolet light is one energy region of the electromagnetic spectrum, which lies between the x-ray region and the visible region. UV itself lies in the ranges of 200 nm to 390 nm. The UV-C range is from 240 nm to 290 nm. Optimal UV germicidal action occurs at 254 nm.

How does UV-C work to kill the micro-organisms?

UV radiation reacts with the DNA and RNA of viruses and scrambles their genetic code so they cannot reproduce, which renders them sterile and, effectively dead.

Dosage:

UV dosage is the most critical function of UV sterilization because the extent of inactivation is proportional to the dose applied to air inside the respiratory tract. A UV LED emits a set amount of ultraviolet energy; it is important that the UV chamber be sized correctively. Contacted time, which is the time allows for the contaminated air within UV chamber to be sterilized by a certain amount of UV dosage. The dosage is the amount of energy per unit area (calculated by dividing the output in watts by the surface area of UV LED), to determine the overall effectiveness of microbial destruction in the system.

UV dose is expressed in microwatt seconds per centimeter squared ($\mu Wsec/cm^2$). Divided by 1000 to express the dose in $mJ/cm^2$). The preferred notation, Dose=time (sec)×output(watts)/area ($cm^2$).

Briefly summarized, of the present idea is directed to a device used to kill the micro-organisms inside the respiratory tract. In one implementation, the device assembly includes a triple-lumen catheter and UV control unit. The distal end of one of the catheter's lumen is a curved UV chamber (for easy insertion and removal), and the proximal end has a cable with a socket to be connected to the UV control unit.

The UV control unit is used to control the shape of UV, for either continuous or pulsed wave based on the application. Also UV the control unit is used to increase or decrease the UV output power. Further, the control unit has a screen to monitor the actual UV output in real time and to issue an alarm in case the output is outside certain limits.

The second lumen of the catheter is used for oxygen supply (uncontaminated fresh air) necessary for treatment.

The third lumen of the catheter is used for suction.

The UV control unit also controls the oxygen supply rate and suction rate via two separate valves on the surface of a UV control unit (not shown for simplicity). An oxygen tube and a suction tube are inserted into each valve cavity to allow the valve to close and open the tube's lumen whenever is required. The oxygen valve controls the oxygen supply time, and the suction valve controls the suction time, to get a suitable contact time between the contaminated air and UV power inside the UV chamber to sterilize the contaminated air. This sterilization process may help the patients to get recovered quickly with less medication and hospitalization.

Also, oxygen supply acts as a cooling media for UV LED to keep its temperature within an acceptable range to avoid any damage to the internal tissues of the respiratory tract.

In another implementation, the device may be used to kill micro-organisms inside the other human tracts and animal tracts with different catheters in size and lumens and with different UV chamber and power.

BRIEF DESCRIPTION OF THE DRAWINGS

The accompanying drawings, which are incorporated in, and constitute a part of the specification, illustrate or exemplify embodiments of the present invention and, together with the description, generally explain the principles and features of the present invention. The drawings are briefly described as follows.

DETAILED DESCRIPTION

Reference will now be made to figures wherein like structure will be provided with like reference designations. It is understood that the drawings are diagrammatic and schematic representations of example implementations, and are not limiting of implementations nor are they are necessarily drawn to scale.

Figure 1:
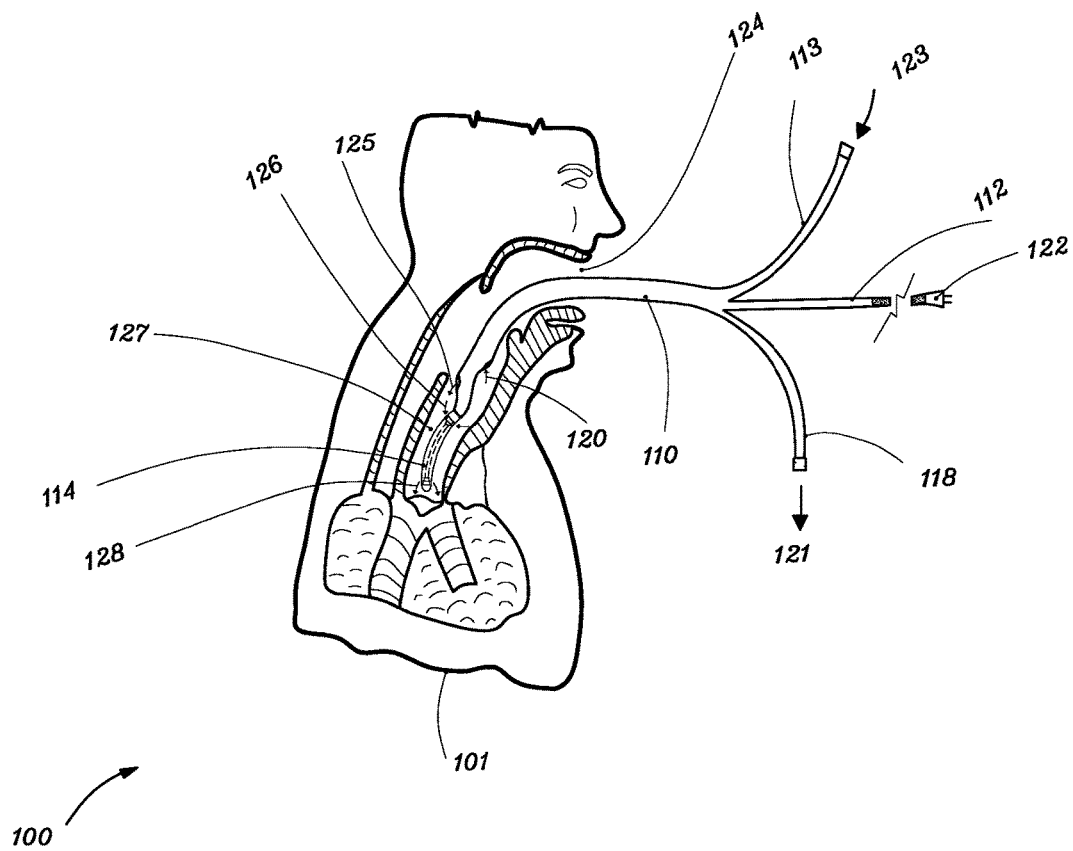
FIG. 1 is a perspective view of inserted device inside the respiratory tract of a patient.

FIG. 1 depicts the feature of implementation of the present idea used for sterilization of contaminated air inside the respiratory tract. It is directly related to a triple lumen catheter 110. A catheter 110 may consist of a suction tube 118 to be used for suction 121. A distal end of a second catheter lumen 112 has a curved UV chamber 114 with UV LED 310 FIG. 3 to sterilize the air inside the trachea 126 of the patient respiratory tract 100.

Figure 2:
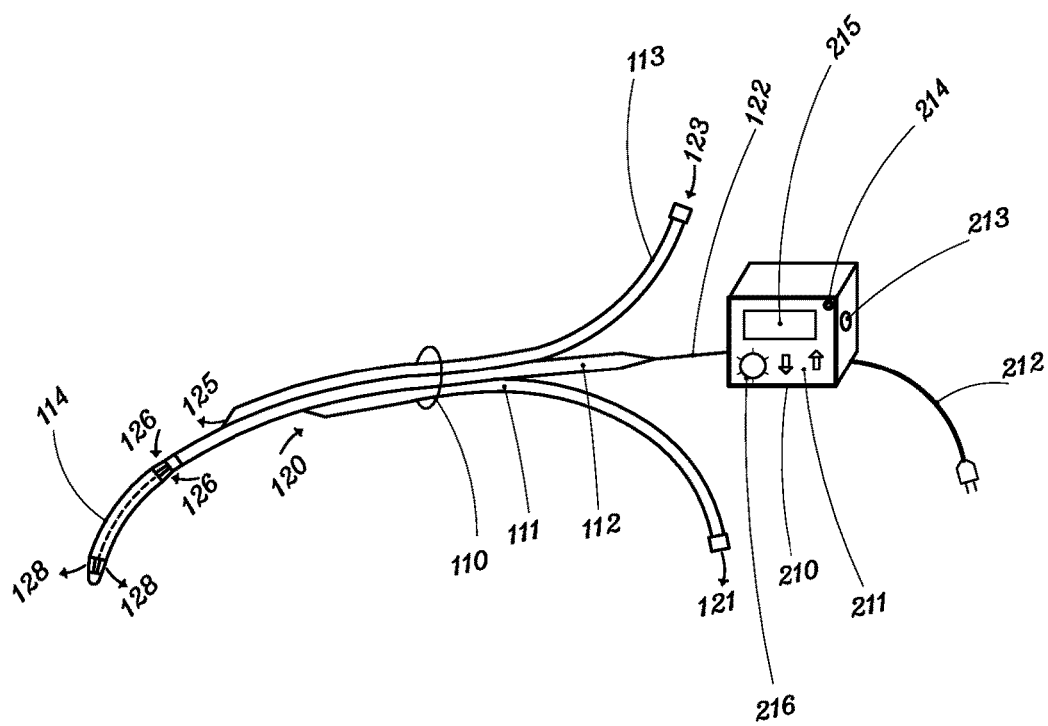
FIG. 2 is a perspective view of a catheter with a curved UV chamber and UV control unit.

The proximal end of the catheter lumen 112 has a cable with socket 122 to be connected to a UV control unit 210 FIG. 2. The third lumen of a catheter 113 is used for oxygen supplies 123.

Figure 3:
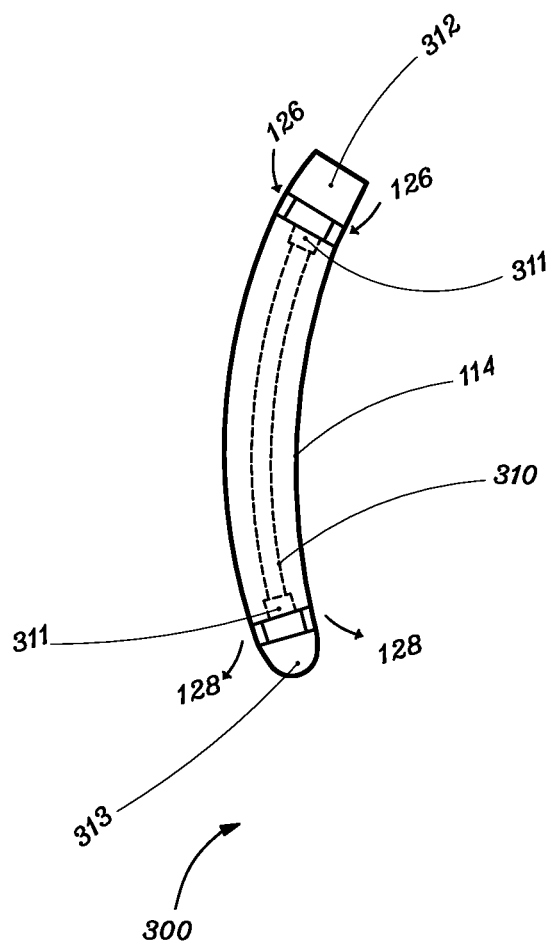
FIG. 3 is a perspective view of a curved UV chamber's components.

UV LED 310 FIG. 3 inside a UV chamber 114 starts to emit UV energy after a power cable with socket 122 is connected to a UV control unit 210 FIG. 2. Oxygen supply 123 inside the oxygen supply lumen 113 exits from an opening 125 inside the trachea 126 and pushes the contaminated air inside the trachea 126 to enter UV chamber 114 via openings 126.

Contaminated air is now exposed to UV energy for sterilization inside the UV chamber 114. Oxygen valve on the surface of UV control unit 210 FIG. 2 (not shown for simplicity) is used to control the oxygen supply rate 113 to give the contaminated air enough time to be sterilized inside the UV chamber 114. When contaminated air is sterilized, an oxygen valve will be opened to allow for oxygen supply to push the sterilized air out of UV chamber 114 via openings 128.

At the same time, the suction valve (not shown for simplicity) will be opened to allow for the suction force 121 to suck the air out of the patient respiratory tract 100 via the opening 120.

The above procedure will be repeated until the contaminated air inside the trachea 126 is completely sterilized.

FIG. 2 shows a catheter with UV chamber and a UV control unit 200, wherein 210 is a UV control unit. Buttons 211 are used to increase or decrease UV output power.

212 is a power cable of a device 210. 213 is an ON/OFF switch for a device 210. 214 is an alarm LED to give flashing light and sound in case of any problem, specifically in case UV power is outside certain limits. 215 is a small screen to monitor the actual UV output power in a real time.

216 is a control knob for continuous or pulsed UV output.

FIG. 2 also shows the catheter's lumens 110, wherein 112 is one catheter lumen with a cable and socket 122 at its proximal end to be connected to UV control unit 210.

The distal end of a catheter lumen 112 is connected to a curved UV chamber 114. A catheter 110 has a second lumen 113 to be used for oxygen supply 123. 125 is the oxygen output opening. Catheter 110's third lumen 111 is used for suction 121 whereas 120 is an air suction inlet.

FIG. 2 also shows a curved UV chamber 114 with its inlet openings 126 and outlet openings 128.

FIG. 3 300 shows the components of a curved UV chamber 114, wherein 310 is UV LED. 311 is a base for UV LED 310 to fix UV LED 310 to UV chamber 114. 312 is the bottom part of a curved UV chamber 114 and 313 is its tip.

The invention claimed is:

1. A device comprising:
    a catheter comprising a first tube, a second tube, and a third tube, wherein the first, second and third tubes extend from a proximal end to a distal end of the catheter;
    a suction opening for providing suction disposed at a distal end of the third tube;
    an oxygen opening for providing oxygen disposed at a distal end of the first tube and disposed distally from the suction opening;
    a UV chamber containing a UV LED disposed at a distal end of the second tube, the UV chamber being curved and comprising air inlet openings and air outlet openings; and
    a control unit connected to the second tube, the control unit comprising an oxygen valve and a suction valve and being configured to control a shape and power of an output of the UV LED and to control the oxygen and suction valves to help move and sterilize contaminated air within the UV chamber.

2. A method comprising:
    inserting the device of claim 1 into a trachea;
    pushing oxygen into the trachea via the first tube;
    receiving contaminated air from the trachea into the UV chamber;
    operating the UV LED within the UV chamber to sterilize the air within the UV chamber; and
    pushing more oxygen into the trachea to remove the sterilized air from the UV chamber.

3. The method of claim 2, wherein the UV LED is in direct contact with the air inside the UV chamber.

4. The method of claim 2, further comprising using a suction mechanism to remove sterilized air from the trachea via the third tube.

* * * * *